United States Patent [19]
Barsamian et al.

[11] Patent Number: 6,073,047
[45] Date of Patent: Jun. 6, 2000

[54] METHOD AND APPARATUS FOR DIAGNOSIS, DETECTION OF CELL ABNORMALITIES AND MORPHOLOGY OF LIVING SYSTEMS

[75] Inventors: Sergei Torous Barsamian; Susan Peter Barsamian, both of Frenchs Forest, Australia

[73] Assignee: Priorsway Pty Ltd, Victoria, Australia

[21] Appl. No.: 08/809,954

[22] PCT Filed: Sep. 26, 1995

[86] PCT No.: PCT/AU95/00646

§ 371 Date: Mar. 27, 1997

§ 102(e) Date: Mar. 27, 1997

[87] PCT Pub. No.: WO96/10740

PCT Pub. Date: Apr. 11, 1996

[30] Foreign Application Priority Data

Sep. 30, 1994 [AU] Australia ................ PM 8516

[51] Int. Cl.⁷ ........................................... A61B 5/00
[52] U.S. Cl. ............................................. 600/547
[58] Field of Search ........................ 600/546, 547, 600/554

[56] References Cited

U.S. PATENT DOCUMENTS

| 4,055,799 | 10/1977 | Coster et al. | 324/71 R |
| 4,220,916 | 9/1980 | Zimmermann et al. | 324/71 R |
| 5,353,802 | 10/1994 | Ollmar | 600/547 |

FOREIGN PATENT DOCUMENTS

| 346968 | 12/1989 | European Pat. Off. |
| 9204630 | 3/1992 | WIPO . |
| 9318402 | 9/1993 | WIPO . |

*Primary Examiner*—Max Hindenburg
*Attorney, Agent, or Firm*—Marger, Johnson & McCollom, P.C.

[57] ABSTRACT

A method and apparatus for dielectric diagnostic analysis of human and non-human cells or tissue functions by measuring the response of the cells or tissue to an applied excitation signal in a time period less than the polarization relaxation time period of a domain group of the cells or tissue under examination.

14 Claims, 12 Drawing Sheets

TABLE 1. RELAXATION TIMES OF CYTOPLASM
OF DOMAINS FOR CELLS OF RAT *, **

| ORGANS | $T_1$ | $T_2$ | $T_3$ | $T_4$ |
|---|---|---|---|---|
| TONGUE | 31.38 | 4.29 | 1.08 | 0.31 |
| HEART | 31.60 | 4.49 | 0.97 | 0.32 |
| SPLEEN | 33.38 | 4.15 | 0.84 | 0.26 |
| LIVER | 34.00 | 4.51 | 1.00 | 0.36 |
| KIDNEY | 27.68 | 4.20 | 0.93 | 0.23 |
| BRAIN | 34.10 | 4.11 | 1.02 | 0.33 |
| MUSCLE | 32.16 | 4.22 | 0.98 | 0.29 |
| SMALL INTESTINE | 34.25 | 4.33 | 1.03 | 0.34 |
| SKIN | 29.70 | 4.18 | 0.89 | 0.31 |

\* AVERAGE DATA FROM TWO RATS.
\*\* OBSERVATION TIME 32 SEC.

FIG.11

TABLE 2. DIELECTRIC PROPERTIES OF TISSUE OF RAT ORGANS *

| SAMPLE PARAMETERS | FRESH TISSUE | | | FIXATED TISSUE | | | | TPV, FRESH TISSUE | | | TPV, FIXATED TISSUE |
|---|---|---|---|---|---|---|---|---|---|---|---|
| | ε AT 1MHz | D$_{MAX}$ | f, [Hz] AT D$_{MAX}$ | ε AT 1MHz | D$_{MAX}$ | f, [Hz] AT D$_{MAX}$ | | 1st DOMAIN | 2nd DOMAIN | MEMB-RAIN | MEMB-RAIN |
| TONGUE | 2580 | 5.55 | 19600 | 83 | 17 | 28000 | | 2.11 | 2.67 | 3.78 | 4.95 |
| HEART | 2380 | 9.76 | 22000 | 80 | 9 | 32000 | | 2.06 | 2.70 | 3.80 | 4.63 |
| SPLEEN | 2155 | 8.39 | 9630 | 71 | 21 | 18800 | | 2.10 | 2.63 | 3.86 | 4.84 |
| LIVER | 1728 | 5.29 | 2840 | 50 | 16 | 30000 | | 2.05 | 2.81 | 3.77 | 5.33 |
| KIDNEY | 1580 | 4.03 | 3460 | 70 | 14 | 25000 | | 2.03 | 2.85 | 4.10 | 5.01 |
| BRAIN | 500 | 17 | 50000 | 65 | 23 | 29000 | | 2.14 | 2.69 | 3.70 | 5.06 |
| MUSCLE | 1300 | 6.88 | 190000 | 67 | 19 | 33000 | | 1.95 | 2.65 | 3.65 | 5.10 |
| SMALL INTESTINE | 1653 | 6.48 | 24800 | 62 | 18 | 26000 | | 2.01 | 2.64 | 3.69 | 5.01 |
| SKIN | 300 | 16 | 170000 | 63 | 21 | 27000 | | 2.03 | 2.65 | 3.57 | 4.90 |

* AVERAGE DATA FROM TWO RATS.

FIG.14

METHOD AND APPARATUS FOR DIAGNOSIS, DETECTION OF CELL ABNORMALITIES AND MORPHOLOGY OF LIVING SYSTEMS

TECHNICAL FIELD

The present invention relates to an apparatus and method of diagnostic measurement and in particular, a method and apparatus adapted to analyse various parameters of living materials and specimens to determine the dielectric characteristic of a specimen under test for the purpose of diagnosis of the state of the specimen. Depending on the specimen, a wide range of states may be susceptible to diagnosis including such as disease in plants, animals or humans; the revelation of residual toxins in consumer goods from dairy products, meat products, fruit and vegetable products, fish, grains and stock feed, oils and other liquids.

The present invention further helps identify abnormalities and transformations in living bodies in their earliest stages, much before the clinical appearance of a disease.

BACKGROUND ART

At the present state of technology it is well known that the dielectric behaviour of such as plant, fruit, animal and human tissue corresponds to broad features in their composition and structure. Recent studies have revealed that the cell is a highly ordered dynamic entity which acts holistically with respect to chemical and physical events within a living body, and the existence of domains in the cytoplasm is a general rule. These domains are electrically polarised units of ordered, packed biopolymers in "biowater". The different organs in a living organism, with compartmental similarity and harmonised metabolism, have basic differences in domain arrangements which lead to a difference in dielectric responses. A disease transformation in a living body which has a viral origin or resulting from the action of toxins and other chemicals also changes the domain structure and hence the polarisation and dielectric response of the tissue or cell.

A domain is herein defined as a region of a system, or a region of a substance, comprising atoms or molecules which can be thought of as a single entity; this single entity being responsive to electric or magnetic fields and includes such a system having a plurality of these entities. Examples of a domain include; a ferroelectric or ferromagnetic domain, a cluster of atoms or molecules, an organic cell, a bacterium, a virus, a cluster or collection of cells.

A domain group is a collection of said domains having the same response to an electric or magnetic field.

In the past, precise measurement of parameters of domains were inconceivable due to limitations of the instruments. Measurements of relative dielectric permittivity, energy dissipation and electrical impedance are not possible due to very high values of electrical conductance overshadowing real kinetic characteristics. Existing methods of measurement are mostly based on impedance bridges, which are inadequate at frequencies below 100 Hz due to noise instability, electrode polarisation and the time required to obtain balanced conditions. These bridges yield relative permittivity, energy dissipation and electrical impedance values only at discrete frequencies and therefore each frequency setting causes disruption of sequential measurements. The dielectric properties of living tissue from bodies will change when they are taken out of their natural environment. Dead tissue will show a greater change with changes of cell morphology. Conductivity measurement is mostly carried out by D.C. electrometers of wide current range, often from $10^{-14}$ Ampere to a few milliAmpere. This range being covered by switching to sequential decade ranges with a mismatch of measured current values. A.C. and D.C. measurements require different apparatus, separate sample settings and long time switching intervals from one instrument to the next. The morphological changes of a cell are much faster, so the obtained parameters will refer to different intracellular structures resulting in an incorrect correlation between these parameters. Sample size limitations sometimes up to a few milligrams reduces electrode sensitivity and field noise overshadows the results for fine structural studies.

DISCLOSURE OF INVENTION

In an effort to ameliorate the disadvantages of the prior art or at least to provide a commercially viable alternative to the prior art, the present invention proposes a dielectric diagnostic analyser (DDA) and a method of diagnosis.

In a first aspect, the present invention consists in an apparatus adapted to perform diagnostic analysis of a specimen having at least one domain group as hereinbefore defined, the apparatus comprising:

excitation generating means to generate a predetermined excitation signal;

measuring means to measure a response signal of the specimen to the predetermined excitation signal:

electrode means for transmitting and receiving the predetermined excitation signal and response signal of the specimen, respectively;

analysing means arranged to analyse said response signal; and switching means adapted to switch the electrode means between the measuring means, and excitation generating means, in a time period less than a polarization relaxation time period of the at least one domain group in the specimen.

Preferably, the excitation generating means is the source of the predetermined excitation signal and may be an electrometer or a frequency bridge adapted to generate a predetermined signal. In one form of the invention the measuring means compares an electrometer or a frequency bridge arranged to measure responses received at the electrode means as the response signals of the system.

Typically the analysing means comprises an electronic computer, electrometer and frequency bridge arranged to analyse the response signals, received at the electrode means and the computer has a display for displaying a diagnostic result. Preferably the switching means is also controlled by the computer which allows switching of the electrode means between the excitation means and the measuring means at times less than the smallest relaxation time, of the polarized domain group, to be measured.

In an embodiment of this invention the electrode means is in the form of a suction cup electrode, a pinch electrode, a thermocontrolled electrode or any combination of two or more similar electrodes.

In a second aspect, the present invention provides a method of diagnostic analysis comprising;

applying a predetermined first excitation signal to a specimen having at least one domain group, as hereinbefore defined, so as to elicit a response from the domain group within the specimen;

analysing the response from the domain group to determine the maximum response of each domain group; and comparing said maximum response to a maximum response of a control specimen.

Preferably the first excitation signal is a ramp function voltage sweep or a time rate of change of voltage, and the response from the domain, in the domain group of the specimen, is measured as a change in a current flow through the specimen over time.

Typically the point of maximum response is at the threshold polarization voltage of each domain group and is representative of a maxima in the polarization of each domain group of the specimen.

Preferably a control specimen is any specimen, analogous to the specimen to be diagnosed and considered to be the statistical norm of that specimen.

In an alternative form of the second aspect of the present invention, the first excitation signal is a frequency dependent applied voltage and the response from the domains is measured so as to allow the determination of dielectric permittivity, and dissipation energy, of each domain group. In this form the point of maximum response of each domain group is determined by a local maxima in the dielectric permittivity or a local minima in the dissipation energy of that domain group.

In a third aspect, the present invention provides a method of diagnostic analysis comprising:

all the steps of the second aspect of the present invention as well as;

applying a second excitation signal corresponding to a signal value at, or near, the point of maximum response of each domain group to elicit a further response in each domain group; and detecting the variation and length of said further response upon removal of the second excitation signal.

Preferably the second excitation signal is applied in the absence of the first excitation signal, and the further response is measured upon removal of the second excitation signal while each domain is relaxing to its natural state.

Typically the detecting of the variation and length of the further response occurs within the time in which the domains in each group relax to the state they were in before the second excitation signal was applied.

BRIEF DESCRIPTION OF DRAWINGS

The present invention will now be described by way of example only, with reference to the accompanying drawings, in which:

FIG. 11 is a table of relaxation time constants for four domains (shows as $\tau_1, \tau_2, \tau_3, \tau_4$) for a plurality of rat organs;

FIG. 14 shows a table of dielectric properties of tissue of rat organs.

BEST MODES

Figure 1:
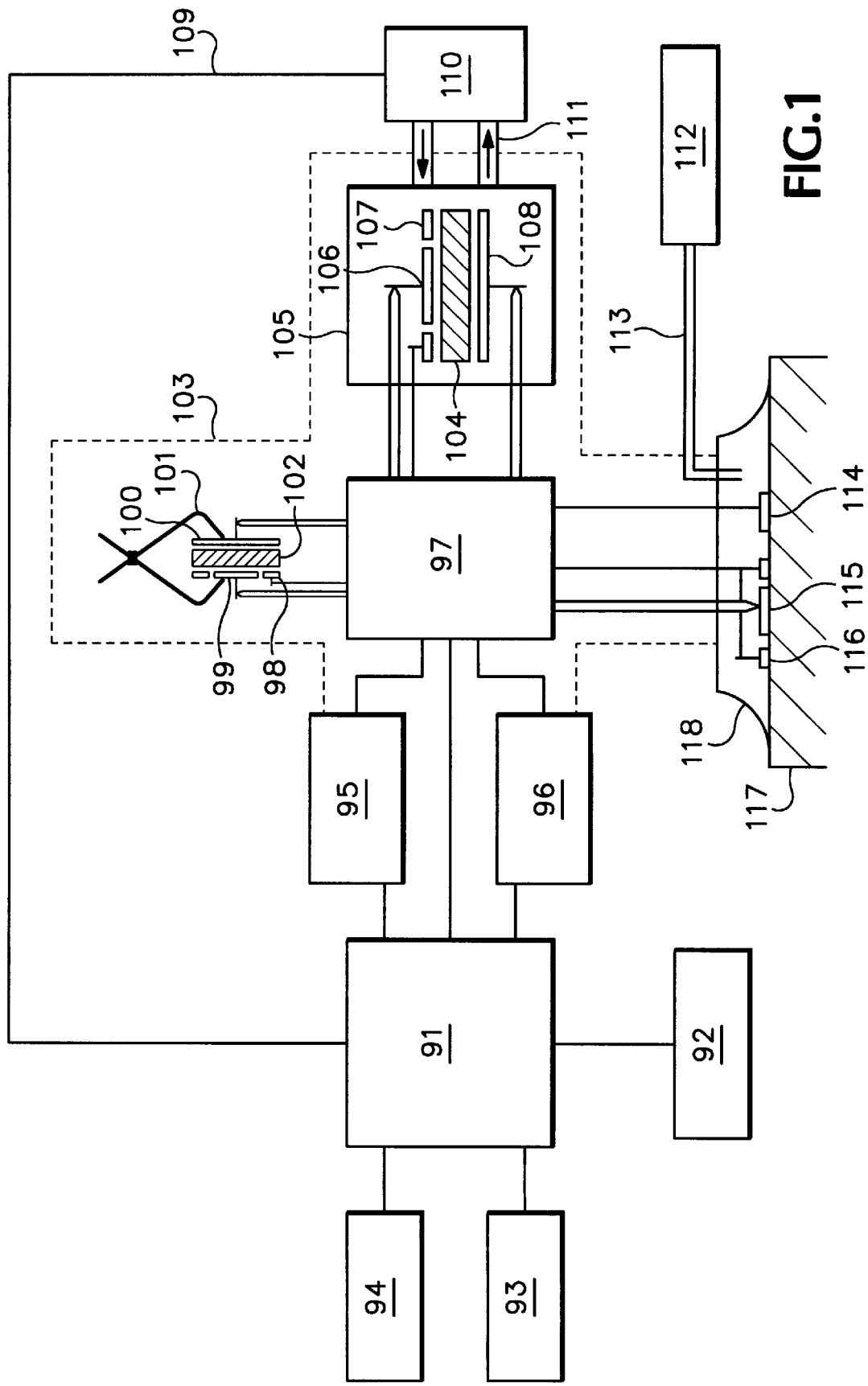
FIG. 1 is a schematic diagram of a dielectric diagnostic analyser in accord with an embodiment of the invention.

FIG. 1 shows an embodiment of the first aspect of the present invention, which comprises a switching means 97 connected to a frequency bridge 95, an electrometer 96 and a computer unit 91 via appropriately shielded cables. The computer unit 91 is also connected to a keyboard 92, a display monitor 93 and a printer unit 94 in the usual way to provide a computer system. The electrometer 96 and frequency bridge 95 are also connected to the computer unit 91, such that an operator can through the use of the keyboard 92 instruct the computer unit 91 to change the settings on the electrometer 96 or the frequency bridge 95. Preferably, the electrometer 96 and the frequency bridge 95 has the additional option of changing the settings manually. The computer unit 91 can be programmed to receive input signals, from the electrometer 96 and the frequency bridge 95, which can be analysed by means of dedicated software programmes such as Intel's IEEE 488 and then to output the resulting analysis on the display monitor 93 or printer 94.

Figure 2:
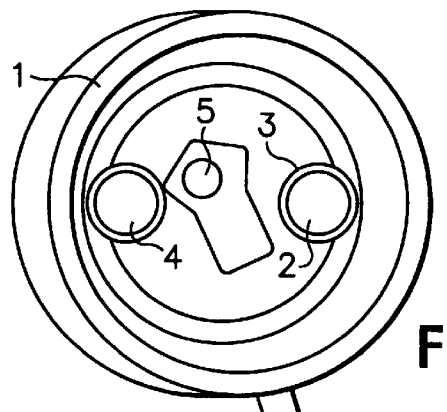
FIG. 2 is a schematic diagram of a preferred embodiment of a suction cup electrode.

The switching means 97 further having connections via a plurality of electrically shielded conducting cables to three electrode devices. The computer unit 91 is programmed to instruct the switch means 97 to switch between any one of the three electrode devices. The first electrode device as illustrated in FIG. 1 and FIG. 2 is a suction cup electrode 118 which comprises an excitation electrode 114 to induce a current in a tissue specimen 117, a measuring electrode 115 to measure the response signals of the specimen 117 resulting from the excitation induced by the excitation electrode 114, a guard electrode 116 to prevent unwanted surface currents reaching the measuring electrode 115, and a suction device 112 connected to the suction cup electrode 118 by way of an airflow link 113 to the air passage channel 125 of the suction cup 118. The suction device 112 is used to adjust the pressure within the suction cup electrode 118, so that not only does the cup adhere to the specimen but the contact pressure between the specimen 117 and the electrodes (i.e. the excitation electrode 114, the guard electrode 116 and measuring electrode 115) can be adjusted to an optimum pressure. The optimum pressure between the electrodes and specimen is obtained from a local maximum value of the dielectric permittivity in a hysteresis plot, as shown in FIG.

Figure 3:
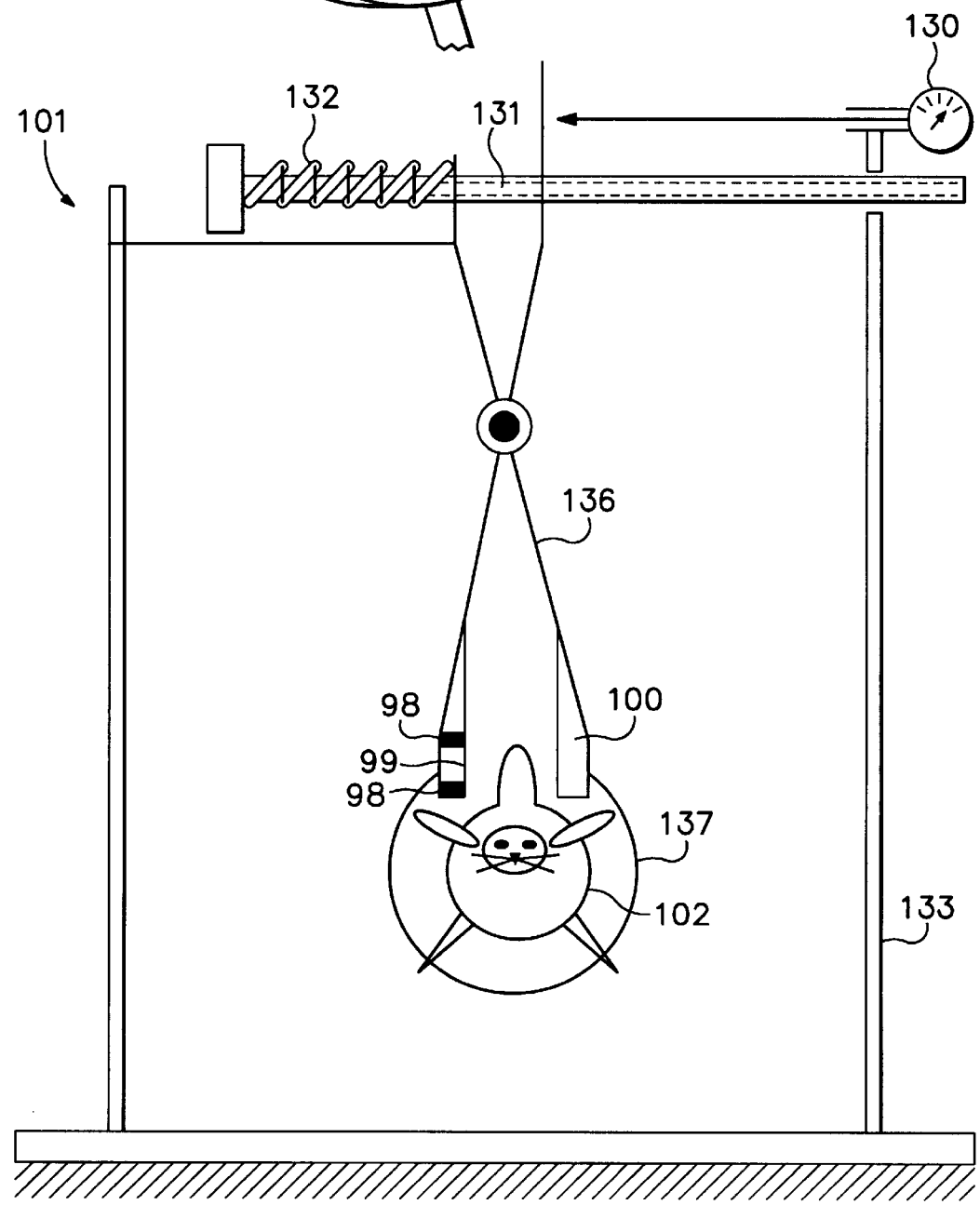
FIG. 3 is a schematic diagram of a preferred embodiment of a pinch electrode.

5. The excitation and measuring electrodes 114 and 115, respectively, are set to the optimum pressure before diagnostic measurements are obtained. The second electrode device illustrated in FIG. 1 and FIG. 3 is hereinafter referred to as the pinch electrode 101 which comprises an excitation electrode 100, mounted on one jaw of a pair of pincers 136, while the guard 98 and measuring electrode 99 are mounted on the opposite jaw of the pair of pincers 136. At the other end of the pair of pincers 136, a spring 132, an adjusting screw mechanism 131 and a micrometer measuring gauge 130 are arranged to adjust and measure the distance between the excitation electrode 100 and the measuring electrode 99 at the jaw end of the pair of pincers 136. A specimen 102 is pinched between the electrodes at the jaw end and a force between the jaws is applied by the adjustment of the screw mechanisms 131 and spring until the desired distance is read off the gauge reflecting the distance between the excitation electrode 98 and the measuring electrode 99 at the jaw end sandwiching the specimen 102 between the electrodes.

Figure 4:
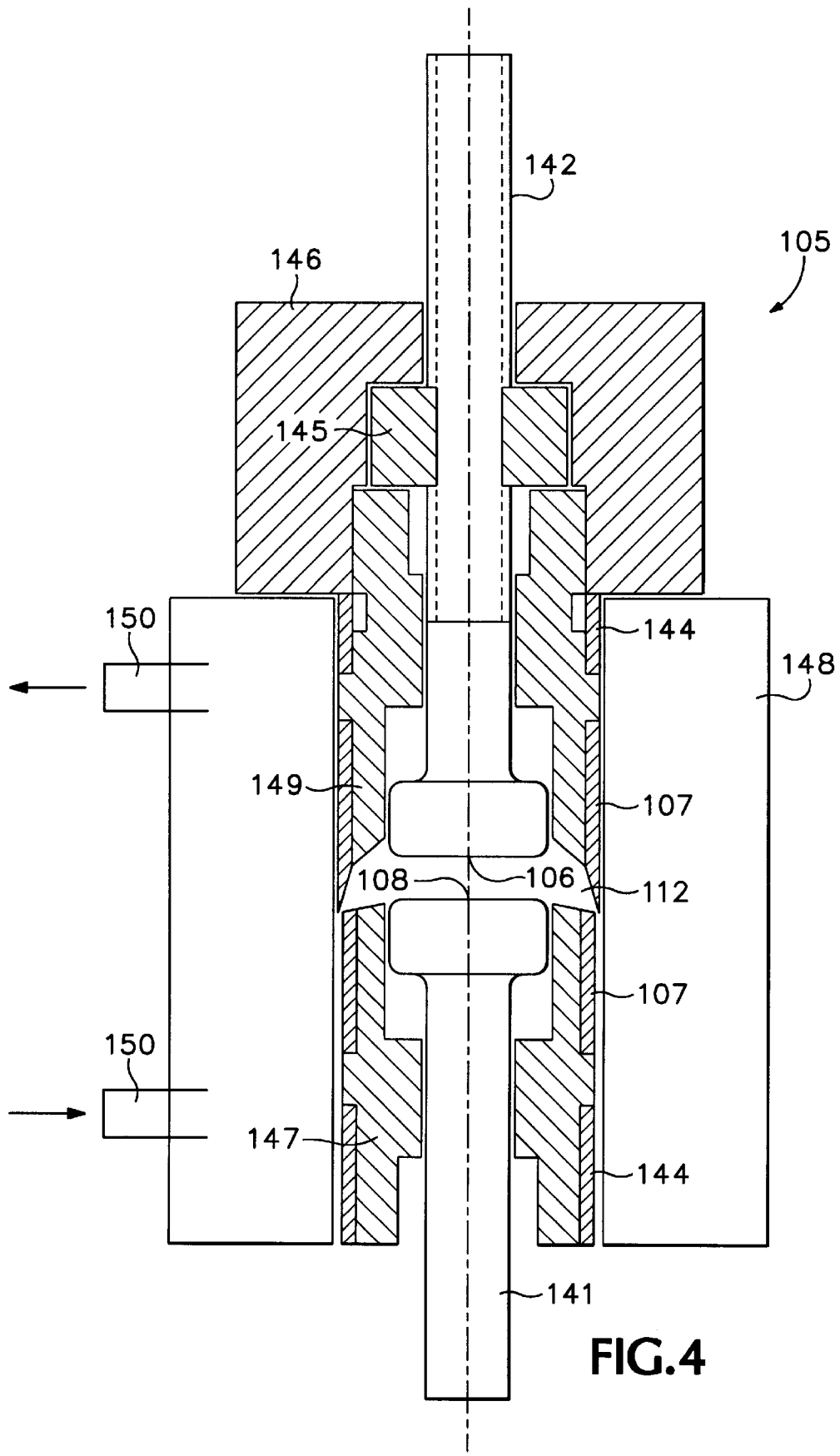
FIG. 4 is a schematic diagram of a preferred embodiment of a thermo-controlled electrode and chamber.
Figure 5:
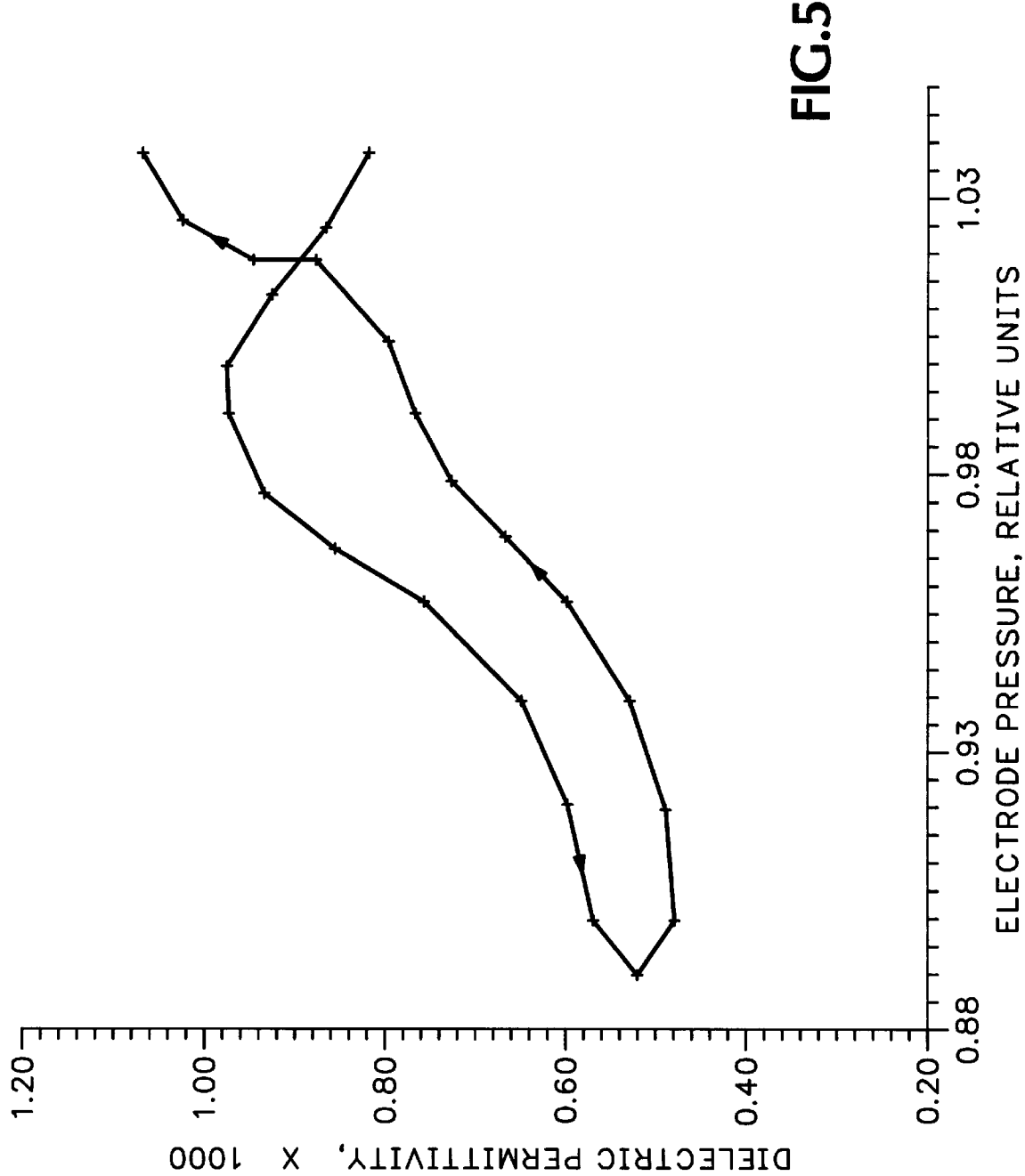
FIG. 5 shows an hysteresis graph of the dielectric permittivity against the applied electrode pressure on living tissue.

The third electrode device illustrated by FIG. 1 and FIG. 4 is hereinafter referred to as the thermocontrolled electrode 105 which comprises a first piston 141, of electrically conductive material to function as the excitation electrode 108, and fits within a first teflon cylinder 147 so that it protrudes from both ends. The said first teflon cylinder 147 has, a guard electrode 107 which wraps around one end of the outer surface of the cylinder 147 and an electromagnetic shield 144 which wraps around the other end of the outer surface of the teflon cylinder 147.

A second teflon cylinder 149 substantially similar to the first teflon cylinder 147, has a second piston 142 functioning as the measuring electrode 106. Piston 142 is allowed to slide in and out of the cylinder 149 by means of an adjusting nut 145 located at the end of the piston 142 which protrudes from second teflon cylinder 149 nearest to the electromagnetic shield 144. A cap 146 placed over the nut 145 stops it from turning at will. The guard electrode 107 on the second teflon cylinder 149 extends beyond the end of the cylinder 149. The two teflon cylinders 147, 149 slide, with some frictional force, into a third cylinder so that the guard electrodes 107 meet, leaving a gap between the excitation electrode 108 and the measuring electrode 106 to fit a specimen 112. The adjusting nut 145 can then be used to change the distance between the gap. The third cylinder being a thermocontrolled jacket 148 with two ports 150 so that fluid can be pumped in or out, at a predetermined temperature, to thermally control the specimen 112. The thermocontrolled jacket 148 is connected to a thermocontrol unit 110 (seen in FIG. 1) by means of tubing to the ports 150. The thermocontrol unit 110 being capable of adjusting the flow rate and temperature of the fluid within the jacket 148. The thermocontrol unit 110 further having a feedback cable 109 to the computer unit 91, so that the flow rate and temperature of the fluid can be set or monitored.

The second aspect of the present invention comprises a method of diagnostic analysis of the human body or specimen under test. The following parameters can be measured directly, or indirectly by way of calculations; current, voltage, specific surface conductance, specific volume conductance, domain relaxation time constants, capacitance, inductance, relative permittivity, impedance, reactance and dissipation factor at different frequencies and temperatures.

Figure 6:
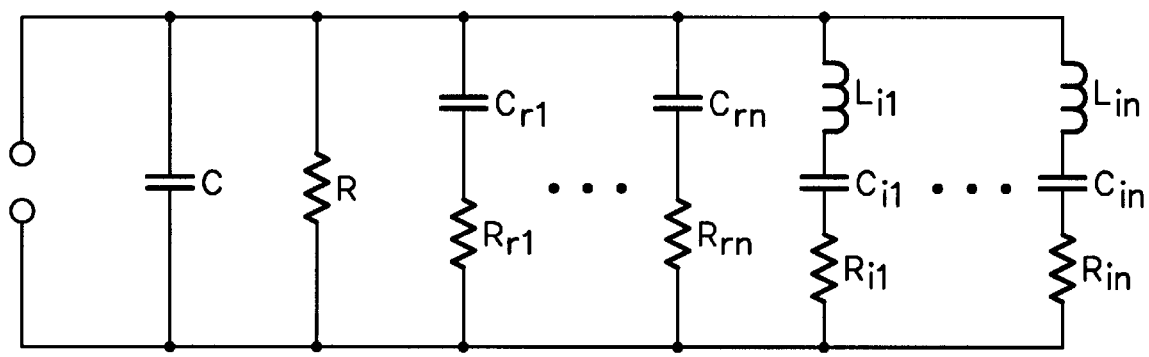
FIG. 6 is a schematic diagram of the equivalent circuit of the inductive, capacitive and resistive processes in the dielectric response mechanism of domain structures analysed by the method and apparatus of the present invention.

FIG. 6 is a schematic diagram of the equivalent electric circuit for the resistive, capacitive and inductive processes in the intracellular morphology based on the known concepts of domain structures.

The embodiment of apparatus of the first aspect of this invention hereinbefore described, enables the measurement of various parameters by exciting the intracellular domains and measuring those parameters within the relaxation time periods of the domains to thereby ameliorate the problem of electrode polarisation obscuring the measurements. Values of these parameters are therefore revealed by measuring these parameters during the relaxation cycle after excitation.

By way of example only, we will demonstrate how the diagnostic results are obtained, for the induction of cancer in a Wistar rat, using the pinch electrode 101 hereinbefore described.

Figure 7:
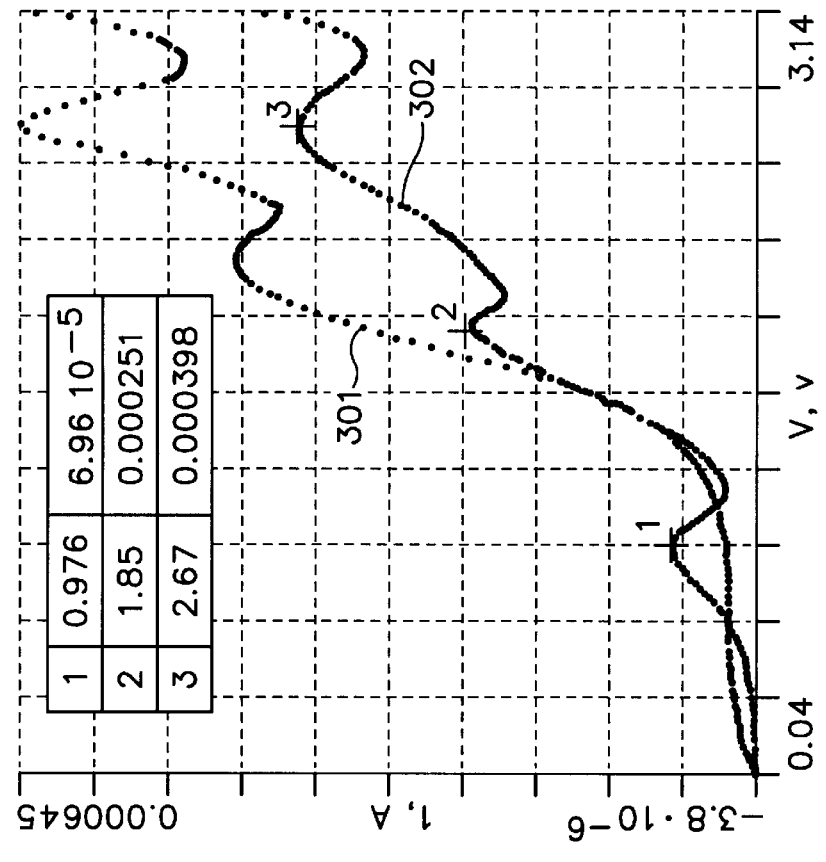
FIG. 7 is the printout of a computer screen of two graphs of current versus voltage each having two plotted curves, the right hand side graph being an enlarged view of a section of the left hand side graph.
Figure 7:
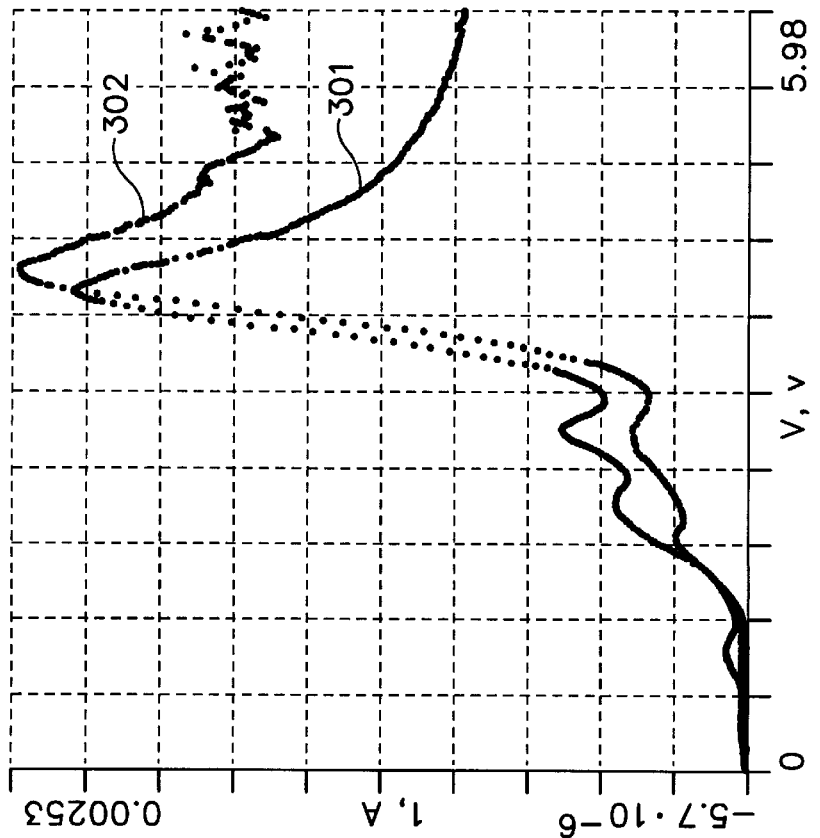

FIG. 7 is a printout of two graphs for the current versus voltage applied to a Wistar rat, the right hand side graph being an enlargement of a section of the curves on the left hand side graph. The curve 301 represents the results of a test on the tongue tissue of a healthy Wistar rat and the curve 302 is a test of the same rat where the tongue was treated with a known carcinogen and cancer was allowed to develop. The diagnosis of cancer follows a series of steps;

In a first step, the initial rate of change of voltage "v" (hereinafter called the voltage sweep rate) and the distance "d" between the excitation electrode 100 and the measuring electrode 99 are assumed. A test run is performed to obtain the current versus voltage graph similar to that of FIG. 7. Numerical data is obtained from the test run and substituted into the following equation to obtain a new voltage sweep rate, and a new electrode spacing amongst other parameters.

$$I(B) = \frac{\upsilon \tau_0}{R}\exp\left(\frac{-B}{dA}\right)\left\{1 - \exp\left[\left(\frac{-B}{d\upsilon\tau_0}\right)\exp\left(\frac{B}{dA}\right)\right]\right\}$$

where I(B) is the current of the function B and $B=E-E_{TPV}$. E the electric field strength, $E_{TPV}$ is the electric field at the threshold polarisation voltage;

"d" the distance between electrodes:

"$\upsilon$" the voltage sweep rate in V/S:

"R" the total resistance of the specimen;

$\tau_o$ is the domain relaxation time constant and $\tau=\tau_o \exp[U/k\ T]$, where U is the activation energy and T the absolute temperature:

"A" is the constant of "softness" which is inversely proportional to the piezomodulus of the polarising unit (domain, cell, etc.).

The test is then set up to the new voltage sweep, the new electrode spacing and the other parameters, to be run again. This first step is repeated until all of the parameters in the above equations converge to their correct values which are determined when the values stop changing substantially after each iteration. Finally, a test run with the correct values is performed and the threshold polarisation voltage relating to each domain group, indicated on the curves in FIG. 7 by the local maxima, is obtained. On these curves a local maxima or humps of a domain group having a threshold polarisation voltage of less than 1 volt is indicative of some abnormality.

Figure 9:
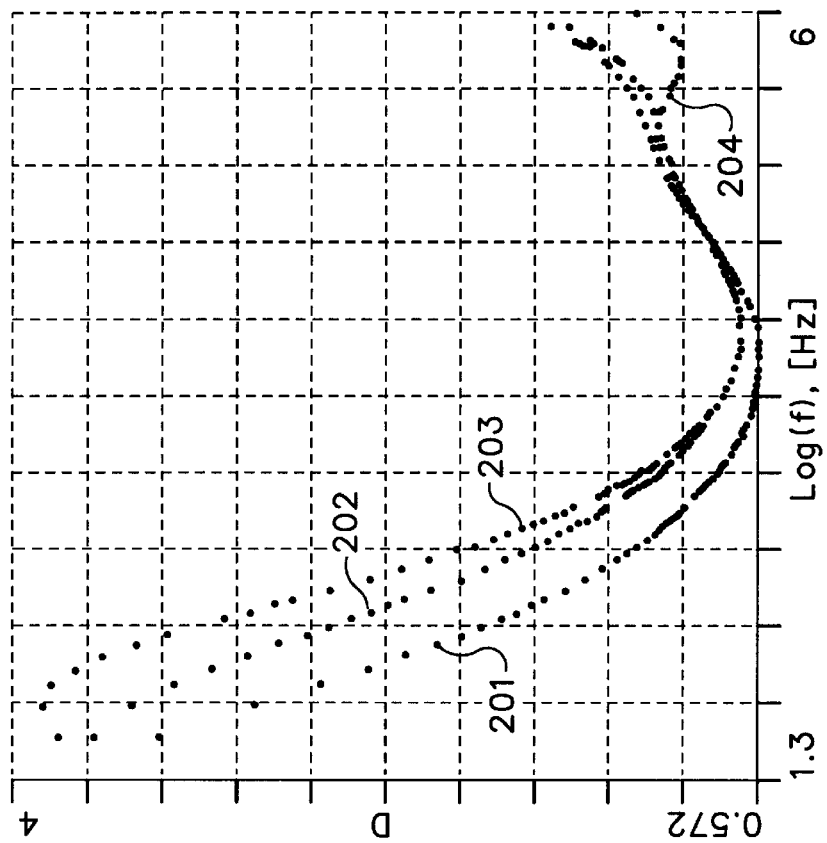
FIG. 9 is a graph containing 3 curves of the dissipation factor versus the frequency on logarithmic scale for a rat.
Figure 8:
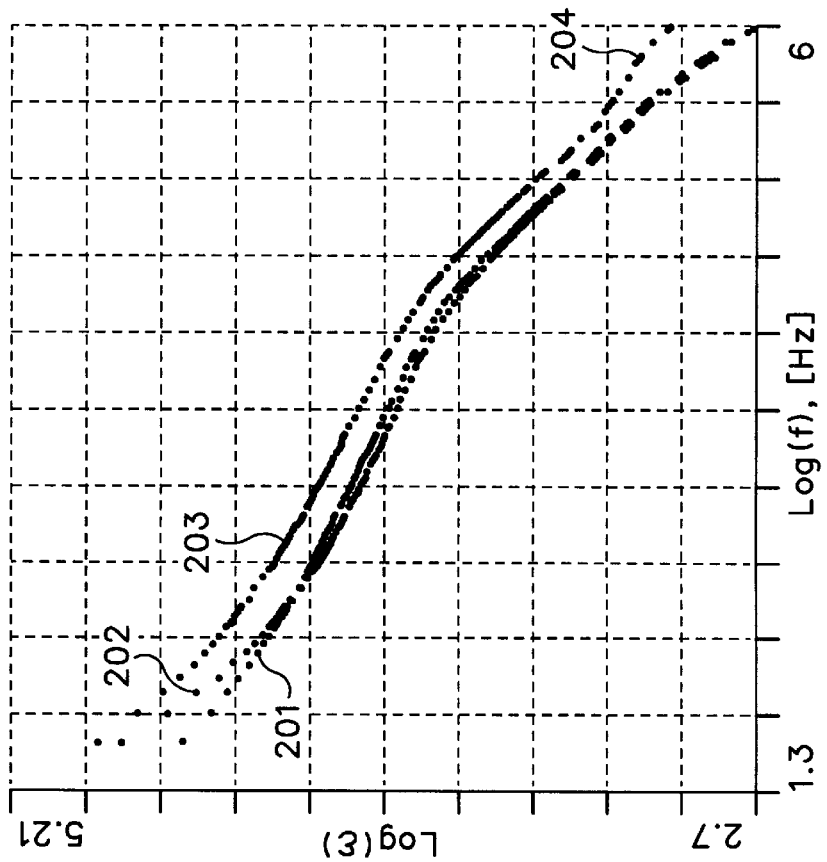
FIG. 8 is a graph containing 3 curves of the relative permittivity versus the frequency for a rat shown on a logarithmic-logarithmic scale.

In a second step the relative permittivity (FIG. 8) and the dissipation factor (FIG. 9) is obtained as a function of the frequency of the applied voltage. In FIGS. 8 and 9 the curve marked 201 is the result of the measurements of a healthy Wistar rat, the curve marked 202 is the result of a Wistar rat with an ulcer and curve 203 is a Wistar rat with cancer which is indicated by the local maxima or hump 204 in the curve.

Figure 12:
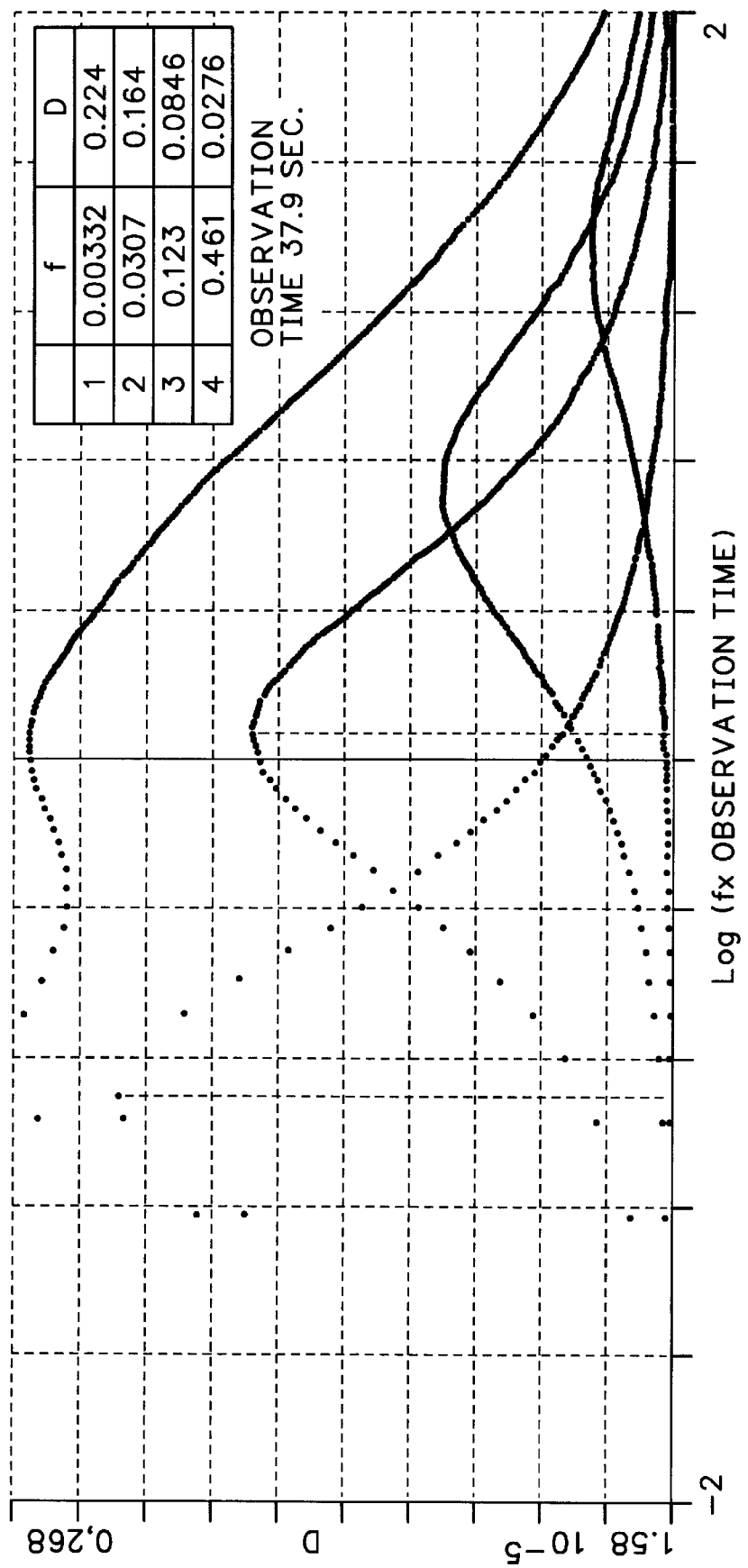
FIG. 12 is a graph of a Fourier analysis of four domains in the intracellular structure of the thigh muscle of a Wistar rat.

In a third step the specimen is excited or charged to the threshold polarisation voltage for each domain independently and allowed to discharge. During this discharge cycle measurements of the discharge current versus time are obtained and analysed to reveal a relaxation time for each domain. A computer software program designed to analyse the relaxation times for each domain is based on the evaluation of the following equations:

$$I(t)=I_o+I_1\exp[-(t/\tau_1)]+I_2\exp[-(t/\tau_2)]+\ldots+I_n\exp[-(t/\tau_n)],$$

where $I_n$ is the current amplitude and $\tau_n$ is the relaxation time constant for the $n^{th}$ polarised domain group. The computer software program cross-checks the results of the relaxation time constants by a Fourier analysis (as an example of the Fourier analysis the dissipation factor D for the thigh muscle of a Wistar rat, see FIG. 12) based on the equation:

$$D(\omega) = \frac{1}{C_\infty}\left\{\frac{\omega C_1\tau_1}{(1+\omega^2\tau_1^2)} + \frac{\omega C_2\tau_2}{(1+\omega^2\tau_2^2)} + \cdots + \frac{\omega C_n\tau_n}{(1+\omega^2\tau_n^2)}\right\}$$

where $C_n$ is the capacitance of the $n^{th}$ domain group, which is related to the current amplitude $I_n$ and the applied voltage "V" by $C_n=I_n\tau_n/V$. C is the sum of the capacitance of each domain group and $\omega$ is the angular frequency ($2\pi f$) for "f" the frequency of the applied voltage "V". $D(\omega)$ is the energy dissipation as a function of the angular frequency.

The experimental determination of the natural frequency of each domain and hence the relaxation time constants, is obtained by the computer software program IEEE 488 from Intel via the measured parameters of the dielectric permittivity and frequency on the basis of the following equations:

$$\epsilon(\omega)=\epsilon_{r1}(\omega)+\ldots+\epsilon_{rn}(\omega)+\epsilon_{i1}(\omega)+\ldots+\epsilon_{in}(\omega)$$

where $$\varepsilon_{rn}(\omega) = \frac{1}{R_m}\left\{\frac{\tau_{rn}}{[1+(\omega\tau_m)^2]}\right\};$$

$$\varepsilon_{in}(\omega) = \frac{1}{R_m}\left\{\frac{\alpha_{1in}}{[\alpha_{1in}^2+\omega^2]} - \frac{\alpha_{2in}}{[\alpha_{2in}^2+\omega^2]}\right\};$$

L. C and R are electrical parameters of the equivalent circuit (FIG. 6) correspond to the electromechanical coupling (piezoelectric like) within the domains in living cell cytoplasm or between living cells in organisms. In the equations above:

$$\alpha_{1in} = -\delta_{in} - (\delta_{in}^2 - \omega_{oin}^2)^{1/2};$$

$$\alpha_{2in} = -\delta_{in} + (\delta_{in}^2 - \omega_{oin}^2)^{1/2};$$

$$\delta_{in} = \frac{R_{in}}{2L_{in}}, \quad \omega_{oin} = \frac{1}{L_{oin}C_{oin}}.$$

The natural frequency is referred to the inductance "$L_{in}$", capacitance "$C_{in}$" and resistance "$R_{in}$" interrelation of the domain following the equivalent electrical circuit in FIG. 6. The resistivity "R" relates to the resistance of each domain group, and $\delta$ relates to the piezoelectric constant. The relative permittivity "$\epsilon(\omega)$" is described in the above equation as a function of the angular frequency, noting that in the equations, the subscript "n" relates to the $n^{th}$ domain group.

Figure 10:
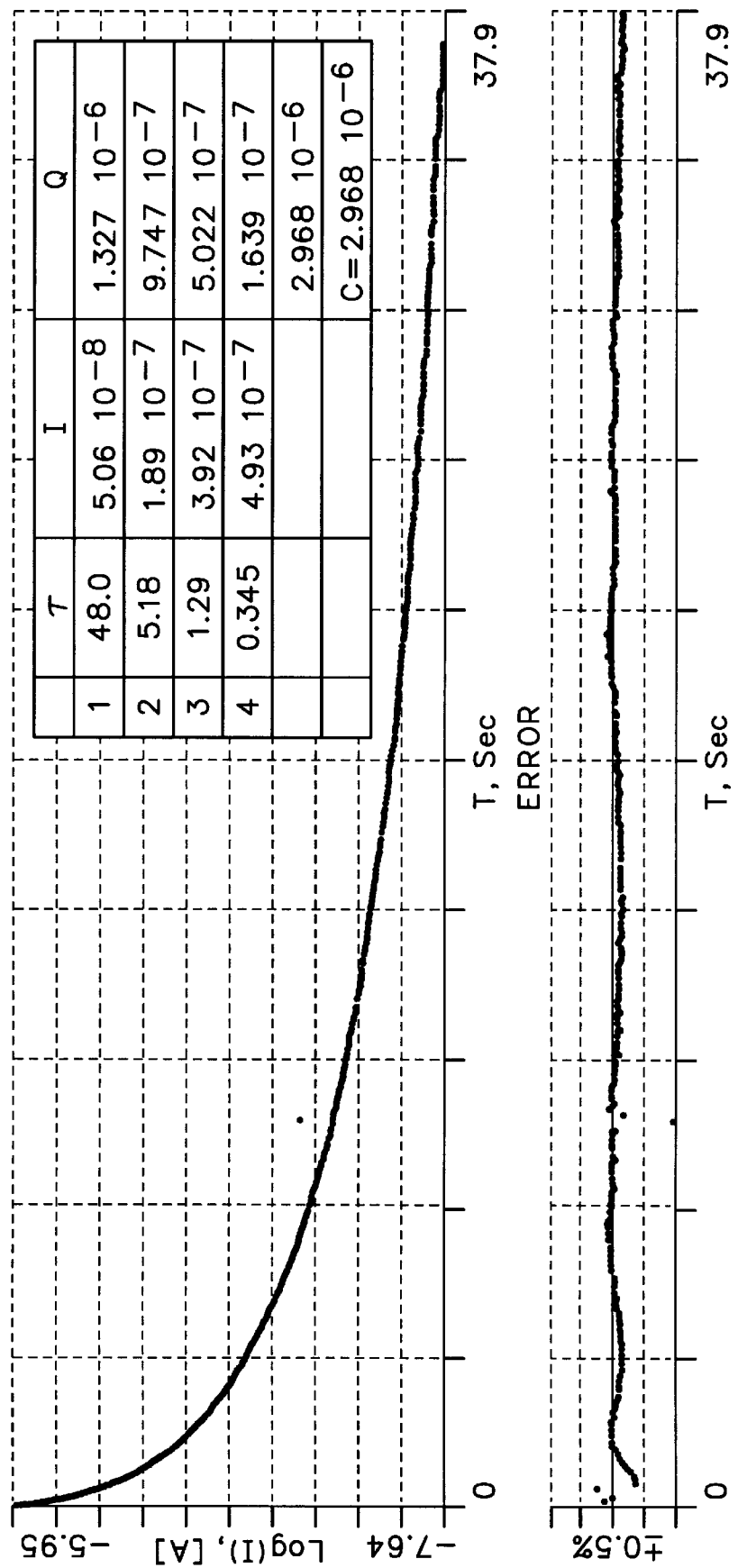
FIG. 10 is an example of discharge current versus time curve for domain structure in a Wistar rat thigh muscle.

FIG. 10 is an example of a discharge current versus time curve for the domain structure in a Wistar rat thigh muscle, however, at the top right hand corner of the figure is a table of relaxation time constants, with corresponding current values and "Q" or charge values for each of four domain structures of the cytoplasm. If the "Q"-values of the discharge processes sum up to give the corresponding value calculated from the input polarisation current, then the test has been successful and the relaxation times of each domain structure correctly reflect the dielectric characteristics of the specimen. These relaxation times are then compared to average relaxation times for a healthy specimen, similar to the table in FIG. 11. If relaxation time constants of the Wistar rat of FIG. 10 are far removed from the values indicated by the table in FIG. 11 then we can surmise with very good probability that there is an abnormality. The abnormality in this case for the Wistar rat of FIG. 10 was cancer.

The third step of the diagnostic procedure is performed within a period less than or equal to the relaxation time period for the domain and preferably within the time frame before any substantial change to the intracellular morphology of the cells of the specimen under test. In the preferred embodiment of the present invention all three steps would be achieved in a few relaxation time cycles.

The DDA as hereinbefore described in the embodiments make possible the recording of the dielectric parameters of tissue samples with minimal invasion. As the domains in cytoplasm are vulnerable to spontaneous ordering, rearrangements or disruption by slight changes, for example by temperature, the simultaneous measurements of parameters make possible the analysis of these changes with reference to the same intracellular morphology.

Figure 13:
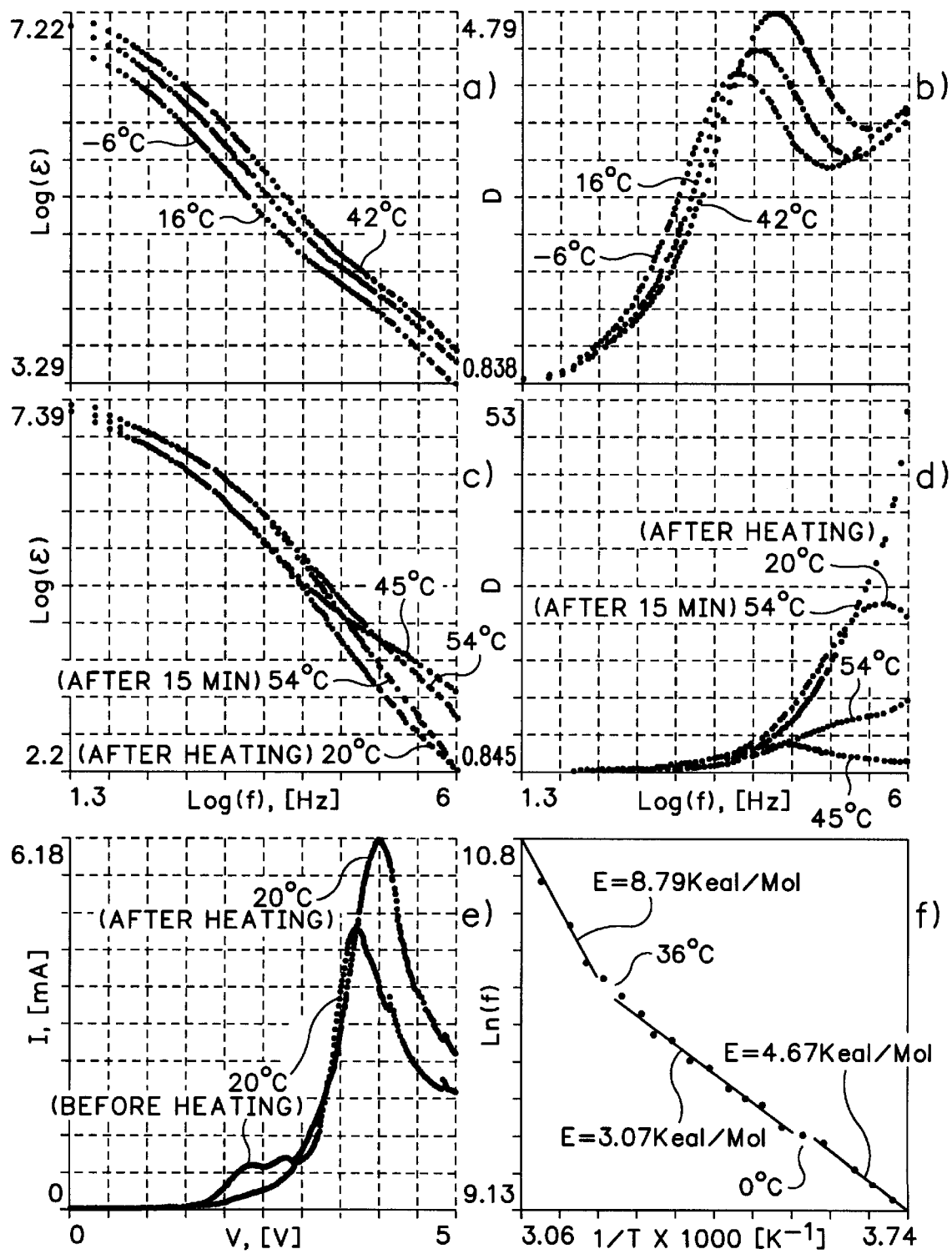
FIGS. 13(a) and (c) are graphs of the dielectric permittivity as a function of frequency, while FIGS. 13(b) and (d) are graphs of the dissipation factor versus frequency: all for various temperature settings of the tongue tissue of a Wistar rat.
FIG. 13(e) is a graph of current versus applied voltage for tongue tissue at 20 degrees Celsius, before and after the tissue was heated above 42.5 degrees Celsius.
FIG. 13(f) is a graph of the frequency response of the tissues versus the inverse of the absolute temperature (temperature measured in degrees Kelvins).

FIGS. 13(a)–(f) relate to the changes of polarisation in the tongue tissue with a change in temperature and FIG. 13(f) shows a comparison of the minute energies required during heating below 41° C.

FIG. 13(e) illustrates the irreversible process that occurs to the dielectric parameters and hence to living tissue (in this case tongue tissue of a Wistar rat), before and after heating the tissue to temperatures above 42.5 degrees Celsius. The process of heating the tissue above a certain temperature "cooks" the tissue. This "cooking" process changes the state of the dielectric parameters of the tissue, compared to the tissue undergoing chemical "fixation" (chemicals such as Kryofix are generally used for optical studies of cellular morphology) which preserves the tissue. These changes in the dielectric parameters are shown in part in FIG. 14.

FIG. 14 is a table showing some dielectric parameters of various tissue samples of rat organs, averaged over two rats, and a comparison of these parameters for fresh or "fixated" tissue.

Industrial Applicability

The dielectric diagnostic analyser (DDA) as described in the embodiments of the present invention also provides a non-invasive, or at least minimally invasive, technique to diagnose changes in the fine structure in cell cytoplasm with respect to the complexity of chemical context. cellular packing, disease transformation and reveal the action of preservation (e.g., Kryofix) and staining (e.g., Haematoxylin) on tissue.

It will be appreciated by a person skilled in the relevant art that this method of diagnostic testing can be applied to any specimen or substance where a domain type structure within cells can be defined including any Maxwell-Wagner system. To study ultrafine structure and intracellular kinetic parameters of cells, including the cell cytoplasm, tissue, organs, the body's metabolic processes, the detection of disease and disease transformation at the onset of said disease including the differentiation of diseases having or not having a viral origin.

The method herein described provides a diagnostic tool which can be adapted to imaging techniques, similar to medical imaging. This diagnostic method and apparatus can be adapted to animals in animal husbandry, plants in agriculture, environmental diagnostics of bacteria and algae in waterways and to chemical analysis of effluent amongst other fields of use. Typically the diagnostic method hereinbefore described is well suited to the analysis of the presence or absence of toxins and other chemicals in specimens such as dairy products, vegetables, meat, fruit, fish, grains, oils, seeds and stock feed products, soil, water as well as viral diseases in plants, animals or human bodies.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. An apparatus adapted to perform diagnostic analysis of a specimen having at least one domain group as hereinbefore defined, the apparatus comprising:

excitation generating means to generate a predetermined excitation signal;

measuring means to measure a response signal of the specimen to the predetermined excitation signal;

electrode means for transmitting and receiving the predetermined excitation signal and response signal of the specimen, respectively;

analysing means arranged to analyse said response signal; and switching means adapted to switch the electrode means between the measuring means, and excitation generating means, in a time period less than a polarization relaxation time period of the at least one domain group in the specimen, the switching means being controlled by the analysing means to switch the electrode means between the excitation means and the measuring means at times less than the smallest relaxation time to be measured.

2. An apparatus as claimed in claim 1 wherein the excitation generating means is the source of the predetermined excitation signal.

3. An apparatus as claimed in claim 2 wherein the excitation generating means is an electrometer.

4. An apparatus as claimed in claim 2 wherein the excitation generating means is a frequency bridge.

5. An apparatus as claimed in claim 1 wherein the analysing means comprises an electronic computer.

6. An apparatus as claimed in claim 1, wherein the electrode means is a suction cup electrode, a pinch electrode or a thermocontrolled electrode.

7. A method of diagnostic analysis comprising:

applying a predetermined first excitation signal to a specimen having at least one domain group, as hereinbefore defined, so as to elicit a response from the domain group;

analysing the response from the domain group to determine the maximum response of each domain group;

comparing said maximum response to a maximum response of a control specimen; applying a second excitation signal corresponding to a signal value at, or near, the point of maximum response of each domain group to elicit a further response in each domain group; and detecting the variation and length of said further response upon removal of the second excitation signal.

8. A method as claimed in claim 7 wherein the first excitation signal is a ramp function voltage sweep or a time rate of change of voltage, and the response from the domain, in the domain group of the system, is measured as a change in a current flow through the system over time.

9. A method as claimed in claim 7 wherein the first excitation signal is a frequency dependent applied voltage and the response from the domains is measured so as to allow the determination of dielectric permittivity, and dissipation energy, of each domain group.

10. A method as claimed in claim 7 wherein the second excitation signal is applied in the absences of the first excitation signal.

11. A method as claimed in claim 7 or 10 wherein the further response is measured upon removal of the second excitation signal while each domain is relaxing to its natural state.

12. A method as claimed in any one of the claims 7, 10 and 11 wherein the detecting of the variation and length the further response occurs within the time in which the domains in each group relax to the state they were in before the second excitation signal was applied.

13. A method as claimed in claim 7, wherein the specimen is of human cells or tissue.

14. A method as claimed in claim 7, wherein the specimen is other than of human cells or tissue.

* * * * *

UNITED STATES PATENT AND TRADEMARK OFFICE
CERTIFICATE OF CORRECTION

PATENT NO.   : 6,073,047                                                Page 1 of 1
DATED        : June 6, 2000
INVENTOR(S)  : Barsamian et al.

It is certified that error appears in the above-identified patent and that said Letters Patent is hereby corrected as shown below:

Column 7,
Line 22, "C" should read -- $C_\infty$ --.

Signed and Sealed this

Fourth Day of November, 2003

JAMES E. ROGAN
*Director of the United States Patent and Trademark Office*